United States Patent [19]

Schneider et al.

[11] Patent Number: 4,618,690
[45] Date of Patent: Oct. 21, 1986

[54] PROCESS FOR THE PREPARATION OF (1S, 4R)-4-HYDROXY-2-CYCLOPENTENYL ESTERS

[75] Inventors: Manfred Schneider, Wuppertal; Kürt Laümen, Monchen-Gladbach, both of Fed. Rep. of Germany

[73] Assignee: Bayer Aktiengesellschaft, Leverkusen, Fed. Rep. of Germany

[21] Appl. No.: 734,421

[22] Filed: May 15, 1985

[30] Foreign Application Priority Data

Jun. 1, 1984 [DE] Fed. Rep. of Germany ....... 3420510
Oct. 30, 1984 [DE] Fed. Rep. of Germany ....... 3439598

[51] Int. Cl.⁴ .......................... C07F 7/08; C07F 7/18; C07F 7/04
[52] U.S. Cl. .................................... 556/441
[58] Field of Search ......................... 556/441

[56] References Cited
U.S. PATENT DOCUMENTS 4,197,245 4/1980 Wissner ........................... 556/441 X
4,202,988 5/1980 Wissner et al. .................. 556/441 X Primary Examiner—Paul F. Shaver
Attorney, Agent, or Firm—Sprung Horn Kramer & Woods

[57] ABSTRACT

Optically pure (1S, 4R)-4-hydroxy-2-cyclopentyl ester of the formula

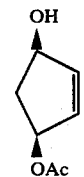

in which
  Ac is an aliphatic acyl radical having 1 to 18 carbon atoms, is produced by contacting a meso such as porcine liver esterase. The products are useful in synthesizing cyclopentanoid products such as brefeldin A, sesquiterpenes and prostaglandins.

4 Claims, No Drawings

PROCESS FOR THE PREPARATION OF (1S, 4R)-4-HYDROXY-2-CYCLOPENTENYL ESTERS

It has been found that (1S,4R)-4-hydroxy-2-cyclopentenyl esters (II) of high optical purity are obtained when meso-cis-1,4-diacyl-2-cyclopentenes (I) are hydrolyzed in the presence of enzymes.

In this context, in formula (I) acyl denotes an aliphatic acyl radical having 1-18, preferably 1-6, carbon atoms. The acetyl and propionyl radicals are of particular importance in this context. The 3-phenylpropionyl radical may also be mentioned in this connection.

A particularly suitable enzyme is porcine liver esterase (P.L.E., E.C.3.1.1.1). The following are also suitable:

α-chymotrypsin (E.C.3.4.21.1)
acetyl esterase (E.C.3.1.1.6)
acetyl esterase (Bac. subtilis)
*Saccharomyces cerivisiae* (baker's yeast)
lipase (*Candida cylindracea*) (E.C.3.1.1.3)
lipase (Rhizopus Sp.)

Remarkably, when the two latter enzymes are used, products having the opposite absolute configuration are obtained.

The enzymes used according to the invention can be employed both in the soluble form and as immobilized enzymes, for example on BrCN activated Sepharose or oxiraneacrylic beads.

Using the process according to the invention, (1S,4R)-4-hydroxypentenyl acetate (II; Ac=acetyl) and (1S,4R)-4-hydroxypentenyl propionate (II; Ac=-propionyl), in particular, can be prepared. The initial products (I) can be obtained in large amounts from low-cost starting materials [C. Kaneko, A. Sugimoto, S, Tanaka, Synthesis 1974, 376]. The compounds II and the derived products like (R)—/(S)—V and VI are valuable building blocks for cyclopentanoid natural products like brefeldin A, sesquiterpenes and prostaglandines [see M. Nara, S. Terashima, S. Yamada, Tetrahedron 36 (1980) 3161 and M. Harre, P. Raddatz, R. Walenta, E. Winterfeldt, agnew. Chemie 94 (1982) 496].

The compounds II can be converted into the other enantiomers (1R,4S) by selective manipulation of the functional groups.

There is a wide variety of possible reactions of the compounds II.

It has been shown, in fact, that treatment of the compounds II with 2,3-dihydropyran/p-TsOH provides (−)-1S,4R)-4-tetrahydropyranoxy-2-cyclopentenyl esters (III). On hydrolysis in the presence of porcine liver esterase, or chemically (NaOH/THF/H2O, R.T.), the latter are converted into (+)-(1S,4R)-4-tetrahydropyranoxy-2-cyclopentanol (IV), which is likewise produced in high optical purity.

Furthermore, the compounds II can be converted into trialkylsilyloxy derivatives (IX) in which the alkyl radical contains 1–5 carbon atoms, or into the tribenzylsilyloxy derivative. Examples for the silyloxy groups in silyl ethers of this type are illustrated by the formulae below:

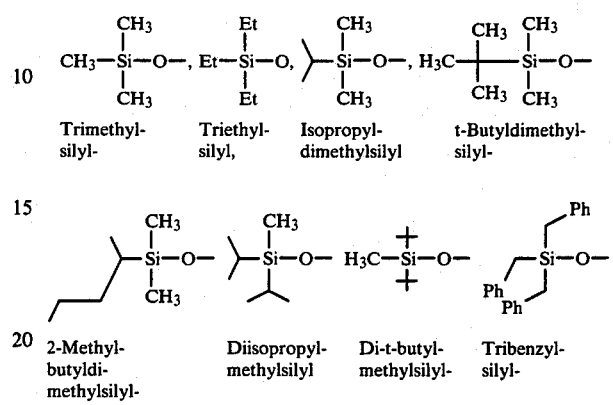

Trimethylsilyl-, Triethylsilyl-, Isopropyldimethylsilyl, t-Butyldimethylsilyl-

2-Methylbutyldimethylsilyl-, Diisopropylmethylsilyl, Di-t-butylmethylsilyl-, Tribenzylsilyl- These compounds are particularly suitable intermediates for the synthesis of cyclopentanoid natural products. The 4-trimethylsilyloxy-2-cyclopentenyl esters and the 4-tert.-butyldimethylsilyloxy-2-cyclopentenyl esters may be mentioned in particular.

Both compounds II and compounds IV can be oxidized by known methods to give (S)-4-oxo-2-cyclopentenyl esters (V) and (R)-4-tetrahydopyranoxy-2-cyclopenten-1-one (VI). respectively.

When the compounds II or IV are subjected to the Claisen rearrangement (triethyl orthoacetate/hydroquinone; 160° C.), then the lactones VII and enti-VII, which are valuable intermediates for the synthesis of prostaglandins, are obtained. VII and ent-VII can be converted by a three step process, via the "Prins" reaction, into the "Corey lactone" (VIII) and its unnatural enantiomer ent-VIII respectively.

The process according to the invention makes it possible to prepare the compounds II, in particular II; R=acetyl, in excellent chemical yields and in initial optical purities which correspond to those in known multi-step processes [K. Ogura, M. Yamaschita, Tetrahedron Letters 1976, 759]. In contrast to elaborate methods for the separation of diastereomers [M. Gill, R. W. Richards, Tetahedron Letters 1979, 1539] or the use, which is equally possible, of the "meso-trick" [M. Nara, S. Terashima, S. Yamada, Tetrahedron 36 (1980), 316], the enantioselective hydrolysis of I; R=acetyl, by the process according to the invention, provides the single enantiomer II; R=acetyl almost exclusively.

This compound is obtained optically pure by straightforward recrystallization.

The reaction scheme below illustrates the conversion I→II according to the invention as well as the further processing of the compounds II obtained.

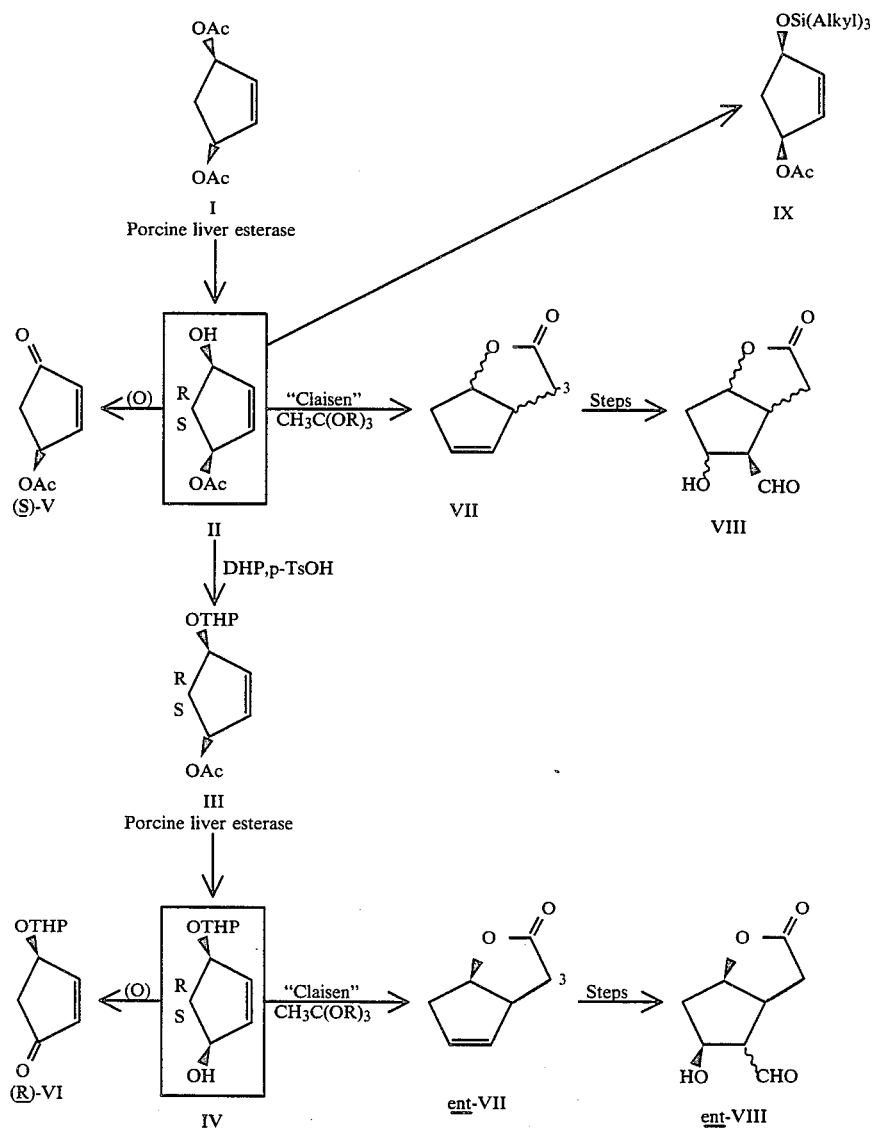

EXAMPLE 1

12.88 g (70 mmol) of meso-cis-1,4-diacetoxy-2-cyclopentene (I; R=acetyl) are suspended in 140 ml of 0.1M phosphate buffer (pH 7) at 32° C. and treated with 1,000 units of soluble porcine liver esterase (P.L.E., E.C.3.1.1.1; 10 mg, standard Bu-O-Ac).

The onset of hydrolysis is indicated by a rapid decrease in the pH. This is kept constant at 7 by continuous addition of 1N NaOH solution from an automatic burette.

After addition of 75 ml (1.04 equivalents) of NaOH, the mixture is extracted with ether.

On fractional distillation, 8.6 g (86% of theory) of analytically pure (−)-(1S,4R)-4-hydroxy-2-cyclopentenyl acetate (II; R=acetyl) are obtained of boiling point 0.2 82° C. and melting point 32°-33° C. The enantiomeric purity was determined by $^1$HNMR [250 MHz-$^1$H-NMR (CDCl$_3$)]δ=1.62 (1H, dt, J=4.15 Hz), 2.03 (3H, s, CH$_3$), 2.50 (1H, bd, J=6.5 Hz, OH), 2.79 (1H, dt, J=7.15 Hz), 4.71 (1H, m), 5.50 (1H, m), 6.05 (2H, AB, J$_{AB}$=(7.5 Hz), and shift reagents, such as Eu (TFC)$_3$, and by gas chromatographical analysis of the (−)-α-methoxy-α-trifluoromethylphenylacetic ester. The ratio of enantiomers is 83:17. (66% e.e.). The angle of rotation is $[\alpha]_{LD}^{20}$ −49.7° (c 0.86, CHCl$_3$).

By recrystallization from petroleum ether/ether (9:1, −15° C.), optically pure [(>95% e.e.) ratio of enantiomers 98:2 (detection limit NMR, Cg)] II; R=acetyl is obtained (63% of theory). Melting point 49° to 50° C. $[\alpha]^{20}$ −68.1°. (c 0.27, CHCl$_3$).

The corresponding reaction of meso-cis-1,4-dipropionoxy-2-cyclopentene (I; R=proprionyl) with the same enzyme, provides, in a yield of 87% of theory, (−)-(1S, 4R)-4-hydroxy-2-cyclopentenyl propionate (II; Ac=propionyl) of boiling point 74° C./0.2 torr. The angle of rotation is $[\alpha]_{LD}^{20}$ −38° (c 0.437, CHCl$_3$). The ratio of enantiomers is 83:17 (66% e.e.). When other enzymes are used with the substrate I; Ac=acetyl, the following results are obtained:

| Enzyme | Abs. configuration | Chemical yield (%) | R:S (% e.e.) |
|---|---|---|---|
| α-Chymotrypsin (E.C. 3.4.21.1) | R | 73 | 71:29 (42) |

-continued

| Enzyme | Abs. configuration | Chemical yield (%) | R:S (% e.e.) |
|---|---|---|---|
| Acetyl esterase (E.C. 3.1.1.6) | R | 79 | 52:48 (4) |
| Acetyl esterase (*Bac. subtilis*, whole organism) | R | 93 | 53:47 (6) |
| *Saccharomyces cerevisiae* (Baker's yeast) | R | 87 | 87:13 (74) |
| Lipase (*Candida cylindracea*) (E.C. 3.1.1.3) | S | 82 | 25:75 (50) |
| Lipase/Rhizopus Sp.) | S | 83 | 17:83 (66) |

Reaction of the substrate I; Ac=propionyl with lipase (*Candida cylindracea*) E.C.3.1.1.3) provides II, Ac=propionyl, with the absolute S configuration, in a chemical yield of 60%, R:S=46:54 (8% e.e.).

II; R=acetyl provides, on reaction with tetrahydropyran and p-TsOH, 95% of theory of (—)-(1S,4R)-4-tetrahydropyranoxy-2-cyclopentenyl acetate (III, R=acetyl) $[\alpha]_{LD}^{20} - 8°$ (c 1.65, CHCl$_3$); this is converted, on treatment with porcine liver esterase under mild conditions at pH 7, into (+)-(1S,4R)-4-tetrahydropyranoxy-2-cyclopentanol (IV). 95% of theory, 1:1 mixture of the distereomrs; $[\alpha]_{LD}^{20}$ 21.5° (c 3.12, CHCl$_3$).

EXAMPLE 2

3.68 g (20 mmol) of meso-cis-1,4-diacetoxy-2-cyclopentene (I; R=acetyl) are suspended in 50 ml of 0.1M phosphate buffer (pH 7) at 32° C., and 20 ml of a suspension of porcine liver esterase immobilized on oxiraneacrylic beads are added.

The onset of hydrolysis is indicated by a rapid fall in the pH. This is kept constant at 7 by continuous addition of 1N NaOH solution from an automatic burette. After addition of 21 ml (1.05 equivalents) of NaOH, the immobilized enzyme is removed by filtration (G3frit). The remaining solution is extracted with ether and the product is fractionally distilled.

2.41 g (85% of theory) of an analytically pure II; R=acetyl are obtained $[\alpha]_{LD}^{20}$ —45.8°, c=1.653, CHCl$_3$.

EXAMPLE 3

5-(S)-acetoxy-3-(R)-trimethylsilyloxy-1-cyclopentene (IX, alkyl=methyl, Ac=acetyl).

1.113 g (7.84 mol) of (1S,4R)-4-hydroxy-2-cyclopentenyl acetate (II, Ac=acetyl) were dissolved in 5 ml of abs. pyridine with the addition of 0.1 g of 4-(N,N-dimethylamino)-pyridine and 20 ml of CCl$_4$. 1.629 g (15 mmol) of (CH$_3$)$_3$SiCl are added dropwise, with stirring, and the mixture is stirred at room temperature for 5 minutes. Then 20 ml of saturated NaHCO$_3$-solution are added, the mixture is extracted by shaking with 50 ml of ether, the organic phase is dried over Na$_2$SO$_4$, the solvent is evaporated off in vacuo, and the residue is distilled in vacuo after addition of a trace of sodium acetate.

Yield: 1.095 g (65% of theory) of a colorless liquid of boiling point 51° C./0.2 torr.

$[\alpha]_{LD}^{20} = -3.6°$ c=4.475 (CHCl$_3$).

In an analogous manner, the compounds of the general formula shown below

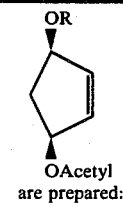

are prepared:

| R | b.p. | $[\alpha]_D^{20}$, CHCl$_3$ | c |
|---|---|---|---|
| Dimethyl-isopropylsilyl | 76° C./0.2 torr | −3.4° | 3.169 |
| Dimethyl-2-pentylsilyl | 107° C./0.2 torr | −2.9° | 4.201 |
| Diisopropylmethylsilyl | 127° C./0.2 torr | −2.5° | 3.870 |
| Triethylsilyl | 121° C./0.2 torr | −3.1° | 3.253 |
| Triisopropylsilyl | 168° C./0.05 torr | −2.0° | 4.139 |
| Dimethyl-tert.-butylsilyl |  | −2.3° | 4.722 |
| Di-tert.-butyl-methylsilyl |  | −1.7° | 4.538 |
| Tribenzylsilyl |  | +0.7° | 3.225 |

It will be understood that the specification and examples are illustrative but not limitative of the present invention and that other embodiments within the spirit and scope of the invention will suggest themselves to those skilled in the art.

We claim:

1. A 4-trialkylsilyloxy-2-cyclopentenyl ester of the formula

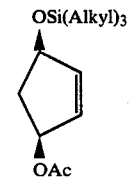

in which the alkyl radical contains 1-5 1 carbon atoms and is optionally phenyl substituted, and Ac is an aliphatic acyl radical having 1 to 18 carbon atoms.

2. An ester according to claim 1, wherein such ester is 4-trimethylsilyloxy-2-cyclopentenyl acetate of the formula

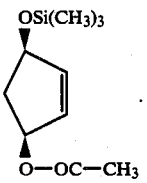

3. An ester according to claim 1, wherein such ester is 4-tert.-butyldimethylsilyloxy-2-cyclopentenyl acetate of the formula

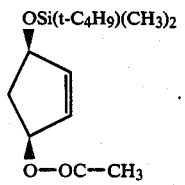

4. An ester according to claim 1, wherein such ester is 4-tribenzylsilyloxy-2-cyclopentenyl acetate of the formula
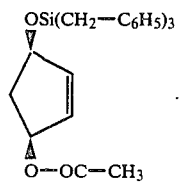
* * * * *

UNITED STATES PATENT AND TRADEMARK OFFICE
CERTIFICATE OF CORRECTION

PATENT NO. : 4,618,690

DATED : October 21, 1986

INVENTOR(S) : Manfred Schneider, et al.

It is certified that error appears in the above-identified patent and that said Letters Patent are hereby corrected as shown below:

| | |
|---|---|
| Abstract, line 1; Col. 1, lines 6, 36, 37, 60, 63; Col. 3, line 60; Col. 4, line 58; Col. 5, lines 21, 26, 51 | Delete "1S, 4R" and substitute --1$\underline{S}$, 4$\underline{R}$-- |
| Col. 1, line 52 | Delete "1R, 4S" and substitute --1$\underline{R}$, 4$\underline{S}$-- |
| Col. 2, line 39 | Delete "enti" and substitute --$\underline{ent}$-- |
| Col. 2, lines 41, 45 | Delete "ent" and substitute --$\underline{ent}$-- |
| Col. 5, line 57 | After "NaHCO$_3$" delete "-" |
| Col. 6, line 42 | After "1-5" delete "1" |

UNITED STATES PATENT AND TRADEMARK OFFICE
CERTIFICATE OF CORRECTION

PATENT NO. : 4,618,690

DATED : October 21, 1986

INVENTOR(S) : Manfred Schneider, et al.

It is certified that error appears in the above–identified patent and that said Letters Patent are hereby corrected as shown below:

Title Page, No. "[75] Inventors:", lines 1-2    Delete "Kürt Laümen" and substitute --Kurt Laumen--

Signed and Sealed this

Twenty-fourth Day of February, 1987

Attest:

DONALD J. QUIGG

Attesting Officer    Commissioner of Patents and Trademarks